(12) United States Patent
Schoeneck

(10) Patent No.: US 8,685,750 B2
(45) Date of Patent: Apr. 1, 2014

(54) HIGH THROUGHPUT SCREENING EMPLOYING COMBINATION OF DISPENSING WELL PLATE DEVICE AND ARRAY TAPE

(75) Inventor: Richard Jerome Schoeneck, Alexandria, MN (US)

(73) Assignee: Douglas Scientific, LLC., Alexandria, MN (US)

( * ) Notice: Subject to any disclaimer, the term of this patent is extended or adjusted under 35 U.S.C. 154(b) by 0 days.

(21) Appl. No.: 12/989,856

(22) PCT Filed: Apr. 28, 2009

(86) PCT No.: PCT/US2009/042007
§ 371 (c)(1),
(2), (4) Date: Oct. 27, 2010

(87) PCT Pub. No.: WO2009/134821
PCT Pub. Date: Nov. 5, 2009

(65) Prior Publication Data
US 2011/0053786 A1    Mar. 3, 2011

Related U.S. Application Data

(60) Provisional application No. 61/048,310, filed on Apr. 28, 2008.

(51) Int. Cl.
*G01N 1/10*    (2006.01)
(52) U.S. Cl.
USPC ......................................................... 436/180

(58) Field of Classification Search
USPC .................................................... 436/180, 47
See application file for complete search history.

(56) References Cited

U.S. PATENT DOCUMENTS

| 5,338,688 A | 8/1994 | Deeg et al. |
| 6,109,717 A | 8/2000 | Kane et al. |
| 6,613,893 B1 | 9/2003 | Webb |
| 2002/0009391 A1* | 1/2002 | Marquiss et al. ............... 422/63 |
| 2004/0022689 A1* | 2/2004 | Wulf et al. .................... 422/100 |
| 2004/0071599 A1 | 4/2004 | Rusch et al. |

FOREIGN PATENT DOCUMENTS

WO    WO2005035110 A1    4/2005

* cited by examiner

*Primary Examiner* — Natalia Levkovich
(74) *Attorney, Agent, or Firm* — Alan Kamrath; Kamrath IP Lawfirm, P.A.

(57) ABSTRACT

High throughput screening is performed by directing an array tape (60) provided with a plurality of wells arranged in rows and columns into a dispensing well plate device (25) having various row and column actuators (40, 50). With the wells containing samples to be tested, activating select ones of row and column actuators (40, 50) of the dispensing well plate device (25), as well causing relative shifting between the actuators (40, 50) and the array tape (60), enables fluid to be dispensed from one or more nozzles of the dispensing well plate device (25) into predetermined ones of the plurality of wells in a wide range of patterns.

13 Claims, 2 Drawing Sheets

HIGH THROUGHPUT SCREENING EMPLOYING COMBINATION OF DISPENSING WELL PLATE DEVICE AND ARRAY TAPE

BACKGROUND

The present invention generally relates to using dispensing well plates (DWP) in combination with array tape.

The goal of high throughput screening is to perform many tests reliably, quickly, and inexpensively.

Reliability is linked to the ability to control process parameters and avoid contamination. For fluid dispensing, volume control is of primary concern. The DWP technology provides exceptional volume control with coefficient of variation (CV) of less than 5%. An example of DWP technology is disclosed in US2004/0074557 A1, which is hereby incorporated herein by reference. Since it is also a non-contact technology, cross contamination is avoided.

The testing speed depends upon the total time of many sequential steps within the process. There are many strategies to reduce the total time such as performing steps in parallel, reducing the cycle time of highly repetitive steps, or changing the process. The DWP technology enables highly parallel dispensing from many positions at once (up to 1536), and the cyclic rate is also quite high (8-9 Hz). It is however important to notice that parallel dispensing from a DWP will have a fixed dispense pattern. For example, it is not possible to simultaneously dispense from an arbitrary subset of DWP wells, and reformat them into a different arbitrary pattern of target wells. A static reformatting can be established within the construction of a single DWP, but variable reformatting in conjunction with parallel dispensing is not possible. The issue of reformatting and particularly variable reformatting is crucial to the process of making combinations.

High throughput screening is the process of performing many tests. The tests are created through manifold combinations of source reagents dispensed and mixed together. The component reagents are supplied in individual containers. The containers commonly take the form of an array of wells or reservoirs. A key concept to grasp is that reformatting is necessary to create all the multiplied combinations. The result will be many target arrays from a few source arrays. The reformatting patterns used can be variable depending upon the needs of the experiment and the number of reagents to be multiplied. These variations will not always factor out nicely within the constraints of a fixed size source array and fixed target array. Using a DWP for variable reformatting requires using less of the highly parallel dispensing and more sequential dispensing. The trend to less parallel and more sequential dispensing decreases speed and therefore increases costs.

SUMMARY OF THE INVENTION

The invention combines a dispensing well plate device having row and column actuators with a tape array in establishing a high throughput screening system. In particular, high throughput screening is performed by directing an array tape provided with a plurality of wells arranged in rows and columns into a dispensing well plate device having various row and column actuators. With the wells containing samples to be tested, activating select ones of row and column actuators of the dispensing well plate device, as well as causing relative shifting between the actuators and the array tape, enables fluid to be dispensed from one or more nozzles of the dispensing well plate device into predetermined ones of the plurality of wells in a wide range of patterns. The overall system enables various screening methods to be employed, including sequential row/column reformatting, parallel row/column stamping with offsetting and various test panel methods. Additional objects, features and advantages of the invention will become more fully apparent from the following detailed description and with reference to the provided figure.

DETAILED DESCRIPTION

Figure 1:
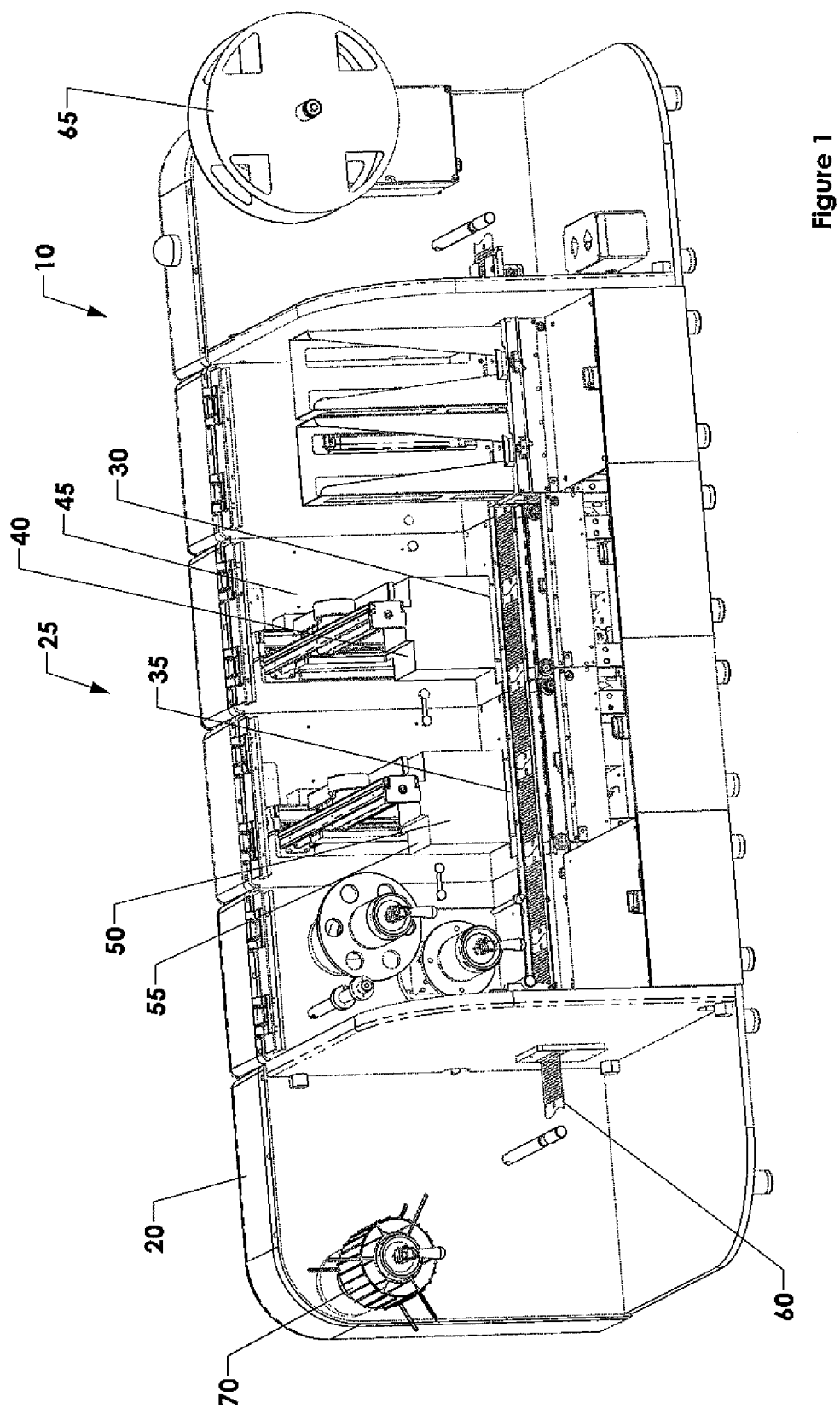
FIG. 1 illustrates a screening unit incorporating both a dispensing well plate device in combination with a tape array.
Figure 2:
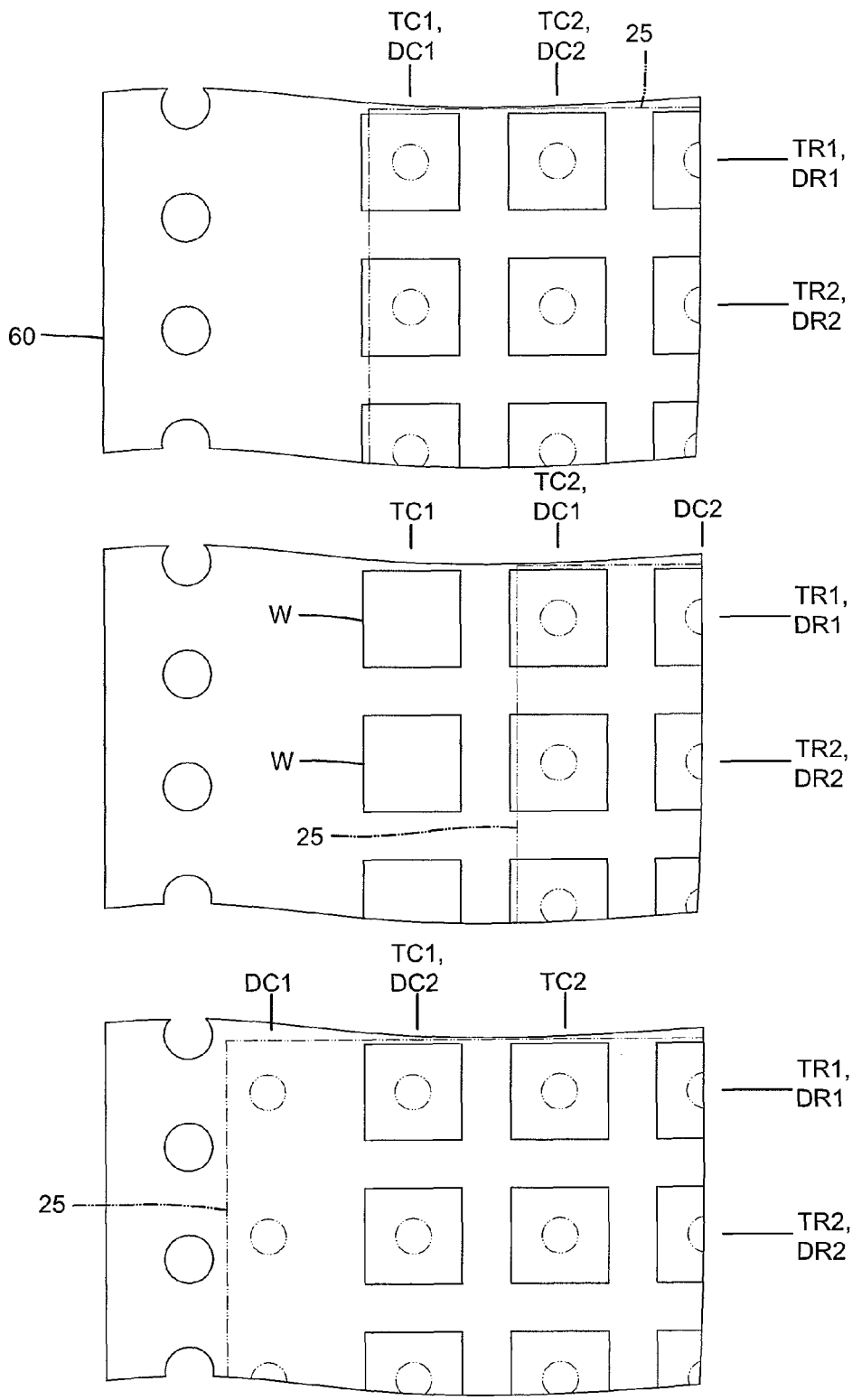
FIG. 2 shows a diagrammatic depiction of dispensing according to the present invention.

With reference to the accompanying figures, a screening unit 10 constructed in accordance with the invention included a housing 20 and a dispensing well plate device (DWP) generally indicated at 25. In the representative embodiment shown, DWP device 25 includes first and second DWP sub-units 30 and 35. As shown, sub-unit 30 includes a respective actuator 40 of a dispenser 45, while sub-unit 35 also includes a respective actuator 50 and dispenser 55. In connection with the invention, DWP device 25 is employed in combination with a tape array 60 which is adapted to be drive from a source reel 65 to a collection reel 70. In general, screening unit 10 is designed to perform high throughput screening by directing array tape 60, which is formed with a plurality of wells W arranged in rows TR1, TR2 . . . and columns TC1, TC2 . . . into dispensing well plate device 25 which can have actuators for various rows DR1, DR2 . . . and columns DC1, DC2 . . . , such as actuators 40 and 50. With the wells containing samples to be tested, activating select ones of row and column actuators 40, 50 of dispensing well plate device 25, as well as causing relative shifting between the actuators 40, 50 and the array tape 60, enables fluid to be dispensed from one or more nozzles (not labeled) of the dispensing well plate device 25 into predetermined ones of the plurality of wells W in a wide range of patterns. The overall system enables various screening methods to be employed, such as based on the manner in which all of the actuators of the dispensing well plate device are controlled and relative movements between the actuators and the tape array as regulated by a controller (not shown), as detailed more fully below.

The following method of reformatting maximizes the use of parallel DWP dispensing. The method shows variable reformatting patterns for test sets of different sizes. It also minimizes consumable costs by using the fewest number of disposable DWPs. The method further discloses how application of these reformatting patterns to an array tape is unique and different from plates. An example of an array tape is disclosed in U.S. Pat. No. 6,878,345, which is hereby incorporated herein by reference.

The process of making combinations can be thought of in terms of multiplication. There are generally two numeric operands, a greater factor (GF), and a lesser factor (LF). The number of tests required to examine every combination is GF×LF. For example, if a laboratory has 10,000 samples they wish to screen against 20 reagents, the GF=10,000 and the LF=20. The number of tests=10,000×20=200,000 screening tests. Another lab may have an experiment with 300 reagents and only 10 samples for 3000 tests. Note that the greater factor can be either the sample or the reagent.

The preferred method for creating combinations using the DWP is to reformat the GF fluids by using row copies, and the LF fluids by using column copies. This basic concept can be practiced through many sequential operations of moderately parallel steps. However, by using offsets, reformat can be done using fewer sequential operations of highly parallel steps. The row/column-parallel-stamping with offsets method creates a very fast but cryptic reformatting pattern which can be readily tracked by computer. There is still another method of reformatting that provides for a single sample to be dispensed onto a 'test panel array'. This method has the benefit of mental simplicity, but at the cost of reduced speed and more consumables. Further, test panels may be pre-loaded by the chemical supplier, relieving the sample/field lab from the costs of organizing and dispensing these test reagents. In the test panel method, the design of the GF DWP can be changed to enable faster loading of the fluids into the DWP by using a single reservoir connected by capillary channel to multiple jets. Also with this change, the GF actuator would be changed to column actuation, just like the LF actuator. The 'test panel' approach can also be used to dispense many samples against a single reagent. This approach is desirable to ensure uniformity of reaction among many samples using the same reagent. Since all the tests are in the same array, they should experience similar processing conditions. Also, the test results are often determined by comparing the values from many samples tested against the common reagent. Three useful methods are thus described: 1) Sequential row/column reformatting; 2) Parallel row/column stamping with offsets; and 3) Test panels.

The following is an example of sequential row and column reformatting: Assume the target array is a 384 well pattern of 16 rows and 24 columns in well tape. The arrays are located at a 144 mm pitch on the well tape. Both the GF and LF DWPs are also in the 384 format. A particular experiment includes 16 assay reagents or single nucleotide polymorphisms (SNP) 'markers' and 2000 samples. This represents a small experiment of just 32,000 tests. Assuming every well in the target tape is to be filled, this experiment will require 32000/384=83.3 or 84 tape arrays. The 2000 samples represent the GF and would be loaded into 384 well DWPs. This will require 2000/384=5.2 or 6 DWPs. The GF plate will be dispensed by making 16 copies of each row. This does not need to take place in any particular fashion, so the first row of the first GF plate could be taken and 16 copies of this row made into the first target array. Then, the first column of the target array would contain 16 copies of the first sample. Now, the LF plate needs to only dispense 16 markers. The LF plate would have the first column filled with the 16 different markers. As the target tape array is aligned with the LF DWP, the first column would dispense into the first column of the target array. Now the first column of the first target array contains one sample compounded with 16 different markers. As the second column of the target array comes into alignment with the first column of the LF DWP, another dispense is actuated. Now the second column of the target contains the second sample compounded with the 16 different markers. This process would continue 24 times until every column of the first target array was complete. This process required 16 row copies and 24 column copies. These actuations are completed sequentially, so the row copy operation would require 16×0.15 seconds=2.4 seconds. The column dispense operation would require 24×0.15=3.6 seconds. The GF row copies can take place sequentially prior to the LF column dispenses, so the cyclic rate would be approximately 2.4+3.6=6 seconds plus 0.4 second delay to advance the next target array into working position, or a 6.4 second total cycle time. The advance of the target relative to the GF and LF DWP is easily accomplished with array tape. This process would repeat by making 16 copies of the second row of the first GF DWP into the second target array. Basically each row of the GF DWPs will translate to one target array. Since 2000 samples did not completely fill the last GF DWP, there will be a partial filling of the 6th GF DWP. There will be 80 wells filled in the 6th GF DWP, or 3 rows plus 8 additional wells in the fourth row. For this fourth row of the 6th GF DWP, the last 16 wells will be empty. As this row is copied into the 84th target array, only the first 8 columns will be filled. So the LF DWP will only need to dispense into the first 8 columns of the 84th target array. Now in this entire experiment, there were 84 target arrays of 24 columns each, or 2016 columns total. A single DWP reservoir will not typically have enough capacity to dispense 2000 times. A volume of 20 ul would be typical in the 384 format, and enough for less than 400 dispense cycles of 50 nl each. Assuming 384 cycles from each well, 2016/384=5.26 or 6 columns of the LF DWP would be required to be filled. The remaining 18 columns could be saved for future experiments. Notice that the LF was sufficient to fill an entire column of the LF DWP. Had there been only 10 LF reagents, the experiment could proceed normally, but with 6 empty rows in every target array. To save consumable costs, the LF reagents could be broken down into sets of eight with a remainder of 2. The sets of eight proceed to fill target arrays completely. The remainder of two would use up a full column of the LF DWP, and the GF DWP would proceed to make two copies of each row to fill out the remainder target arrays. It will always be preferable to use multiples of 16 over 8, over 4, etc. in order to maximize the utilization of the target arrays.

With reference to the previous experiment, the parallel row/column stamping with offsets will now be outlined. It is not necessary to make 16 copies of the first row in the first target array. The speed of the GF dispense could be doubled by making 8 copies of the first two rows. The second target array would also contain 8 copies of the first two rows, but offset by one row. The LF column would be dispensed into these two target arrays as normal. This multiplication scenario creates all of the same combinations as the first scenario, but with twice the speed on the GF station. The total time would reduce to 1.2+3.6+0.4=5.2 seconds, a 20% improvement without adding any consumable costs. This also could be done with the LF dispenser. Taking this to the extreme, one dispense from the GF DWP could be made on the first target. Then in the second array, rows 1 thru 15 are dispensed into target rows 2 thru 16. Then the GF is quickly moved into position to dispense row 16 into target row 1. Then at the LF dispenser, all 6 source columns are dispensed into the first 6 columns of the target. The tape would advance until the next 6 columns would dispense, etc until all 24 columns were filled using 4 dispense cycles. Now the cycle time is not as limited by the dispensing times, but rather the physical limitations of moving the GF dispenser and advancing the tape. In this case, the GF dispense time would be 2×0.01=0.02 seconds. The LF dispense time would be 4×0.01=0.04 seconds. The refill time of 0.14 seconds per dispense would easily take place while the tape is advancing to the next dispense position. Assuming a move of 6 columns=6×4.5 mm=27 mm distance in 0.14 seconds, provides a speed limit of 27/0.14=192.8 mm/sec. The dispense time of 0.01 second× 192.8 mm/sec=1.93 mm travel during one dispense. It is possible to move the tape this fast, and the timing of the LF actuation could anticipate the trajectory of the dispensed droplet. The motion of the GF dispenser could move across the 16 row 72 mm distance in 0.5 seconds without difficulty. Preferably, the tape feed path is provided with slack between the GF and LF stations such that the tape in the GF station stops just long enough to dispense and move across and dispense again while the LF station runs the tape continuously at a speed of approx 200 mm/sec. The cycle time would then be 144/200=0.72 seconds per array. After 16 target arrays are filled, the first GF DWP will be finished. There will be an additional delay of unloading the first GF DWP from the actuator, and loading the second. The load/unload process will need to be very fast, on the order of 1 second. This delay will be amortized over each 16 target arrays, or a slow down of 0.06 seconds per array for an average cyclic rate of 0.80 seconds per array. This more parallel approach is much faster than the first approach by 6.4/0.80=800%! At such high array feed speeds, tape has a clear benefit over plates. When the LF DWP is performing offset dispensing, it is possible to overlap two different target arrays and dispense into both at the same time. The position coordination of the two target arrays for overlap dispensing is easily accomplished using array tape.

These principles can easily be applied to larger experiments. The GF side simply requires more plates to contain the full sample set. The LF side also increases easily by multiples of 16. If the LF set is not a multiple of 16, the additional rows are simply left empty and the process run as if they were filled. But another method allows breaking the experiment into sets of 8, or sets of 4. Taking the example of LF=4 and GF=2000. Load the first column of the LF DWP using four copies of the four reagents to fill up the 16 wells. The GF DWP will dispense as before, but it will only require four target arrays and four offsets to complete all the combinations. The speed will not be diminished except by how many columns are needed to support the full experiment. The total experiment will require 4×2000=8000 tests using 21 target arrays. This requires 21×24=504 column dispenses from the LF, so only 2 columns of the LF DWP will be necessary. This is not a large expense considering it would take this many wells anyway to develop the necessary volume for 8000 tests. Therefore, the consumable cost is not increased. With dispensing from only 2 LF columns, the maximum cyclic rate would be 9 mm/0.15 seconds=60 mm/sec. This would translate to a speed of 144/60=2.4 seconds per array. This time could easily be decreased by using more columns of the LF DWP. This determination requires the tradeoff calculation between utilization costs and material costs.

In the test panel method, there are two preferred variations. The simplest and most preferred is where all wells of a target array contain the same test reagent. Then, the sample DWP performs a single dispense into the target array. The next tape array is filled with a different test reagent. The sample DWP again makes a single dispense into the target array. In this preferred scenario, a number of tape arrays are prefilled with any number of tests. For example, if a lab identifies 11 tests they wish to perform on every sample, they would use test strips of eleven arrays. The pattern of 11 arrays would simply repeat to create many test strips on a single large spool. The spools of test strips may be made in the lab or by the reagent supplier. It is easy to see how this approach can be extended to high numbers of tests and with extreme dispensing speed. The main limiting factor is the speed at which the tape is advanced and the DWP refill time. The refill time of 0.14 seconds per array would allow a tape speed of over 1 meter per second. At this speed, the dispense time of 0.01 seconds would cover a distance of 10 mm. This is much larger than a target well, so it will be necessary to stop or slow down the relative motion long enough to allow the dispensed fluid to hit the target wells. Reciprocating the motion of the DWP actuator is one solution to keep the tape speed high, but this adds to the cost and complexity of the apparatus. Calculating a tape advance move of 144 mm in 0.20 seconds requires a top speed of 950 mm/sec at an acceleration of 2.0 G. So it is possible to dispense 5 arrays per second using this method in tape, a non-practical cycle rate using individual plates as, even with a flight chain or belt, there would be a very real problem of inserting and removing plates from the mechanism at those rates. Using a spool of tape to unwind, feed, and then rewind again, however, provides a solution. The actual throughput is limited by the process of loading and unloading the sample DWP actuator. However, a second sample DWP dispensing station could be added so that one of them is loading while the other is dispensing. Another practical limitation is the spool size. If a source spool has a practical upper limit of say 500 arrays, it will only require 100 seconds to fill an entire spool. Then, the operator or an automated spool loading mechanism would need to load a second spool and remove the first.

The second variation of test panel uses many tests. For example: 384 different tests in a single target array. In this case, a sample DWP using a column actuator would be used. The DWP would be constructed with a single reservoir per column. The samples would be loaded onto the sample DWP and reformatted through capillary action to the entire column. Then, the sample is dispensed using sequential column copies. For higher speed, the lab may choose to use column stamping with offsets, but with the more complicated reformatting pattern. One potential benefit of this approach is the ability to load the sample DWP through mechanical placement of the original sample prep vial and use capillary action of the DWP to distribute the sample to multiple nozzles. This avoids the potential for cross contamination of pipetting while loading the sample DWP. It also avoids the time and expense of pipette washing while loading source DWPs. This approach can be scaled down to use a test panel smaller than a full array. Each test panel would preferably use a fixed number of columns. This multiple does not need to exactly match the array boundary. The test panel may be created using a parallel column dispense from a second DWP actuator. This method is very similar to the parallel row/column stamping with offsets, but with the difference that the sample DWP is using column actuation of the same sample to create a different reformatting pattern.

These three methods of using the DWP in combination with tape address the issues of reformatting and variations in LF and GF values to support experiments of many sizes. The tradeoff between speed and cost can be calculated per lab based upon current costing rates. The actuator apparatus and DWP apparatus remain a constant throughout all these variations. The test panel method has the most speed potential, but prefers experiments of larger LF and GF. The parallel row/column stamping with offsets represents a high speed potential, and more flexibility for smaller experiments. The sequential row/column reformatting method is slower, but enables smaller LF and GF while saving consumable costs. In the higher speed methods, the practical limitations of advancing the target arrays is practically achieved by using array tape in accordance with the invention.

Based on the above, it should be readily apparent that the invention has various applications, particularly in connection with pharmaceutical and biotechnology research. Rather it is important to recognize that the use of row and column actuators of a dispensing well plate device in combination with an array tape provides extraordinary flexibility in dispensing options, as well as the potential for an extremely high operating speed. Once the GF and LF factors are known, a computer algorithm or look-up tables can be employed to automatically establish the best operating approach from those described above based on whether one was interested in maximum speed, minimal consumable use or something there between. The ability to readily move the tape relative to the actuators and/or move the actuators relative to the tape in accordance with the invention simply provides an enormous range of flexibility, particularly based on combined, synergistic results. In any case, although described with reference to preferred embodiments of the invention, it should be understood that various changes and/or modifications can be made to the invention without departing from the spirit thereof. In general, the invention is only intended to be limited by the scope of the following claims.

The invention claimed is:

1. Method comprising:
providing a dispenser containing a plurality of different first reagents arranged in first and second columns and first and second rows defining a first array;
providing first and second targets including wells arranged in first and second columns and first and second rows defining a second array and including second reagents, with the first and second columns and the first and second rows of the first array corresponding to the first and second columns and the first and second rows of the second array;
aligning the dispenser with the first array of the first reagents with the wells of the first target and actuating the dispenser to dispense the first reagents into the wells of the first target;
moving the first and second targets relative to the dispenser in a direction parallel to the first and second columns of the first and second targets; and
aligning the dispenser with the first column of the first array of first reagents with the second column of the wells of the second target and actuating the dispenser to dispense the first column of first reagents into the wells of the second column of the second target.

2. The method of claim 1 further comprising:
aligning the dispenser with the second column of the first array of first reagents with the first column of the wells of the second target and actuating the dispenser to dispense the second column of first reagents into the wells of the first column of the second target.

3. The method of claim 2 wherein providing the first target comprises providing a plurality of different second reagents arranged in the first and second columns and the first and second rows.

4. The method of claim 3 further comprising:
aligning the dispenser with the first row aligned with the second row of the wells of the second target and actuating the dispenser to dispense the first row into the second row of the wells of the second target; and
aligning the dispenser with the second row aligned with the first row of the wells of the second target and actuating the dispenser to dispense the second row into the first row of the wells of the second target.

5. The method of claim 1 wherein providing the first and second targets comprises providing a carrier tape including the first and second targets.

6. The method of claim 1 wherein providing the dispenser comprises providing a dispensing well plate containing the plurality of different first reagents and including actuators; and wherein actuating the dispenser comprises actuating the actuators to dispense the first reagents from the dispensing well plate.

7. The method of claim 1 wherein providing the dispenser comprises:

providing a dispensing well plate including a plurality of nozzles arranged in the first and second rows and the first and second columns of the first array;
providing the first reagents in a prep vial;
placing the prep vial relative to the dispensing well plate with the plurality of nozzles located in the first reagent; and
drawing the first reagents from the prep vial to at least one of the plurality of nozzles of the dispensing well plate.

8. The method of claim 7 wherein drawing the first reagents comprises drawing the first reagents from the prep vial to the nozzles of the first column of the first array.

9. Method comprising:
providing a dispenser with a plurality of different first reagents arranged with a first spacing between the different first reagents and in a column;
providing a dispenser with a plurality of different second reagents arranged with a second spacing between the different second reagents and in a row;
providing first and second targets each including wells in an array having first and second columns and first and second rows, with the wells in the first and second columns being spaced the first spacing of the first reagents and the wells in the first and second rows being spaced corresponding to the second spacing of the second reagents;
aligning the dispenser with the column of the plurality of different first reagents with the first column in the first target and actuating the dispenser to dispense the first reagents into the first column in the first target;
aligning the dispenser with the column of the plurality of different first reagents with the second column in the second target and actuating the dispenser to dispense the first reagents into the second column in the second target;
aligning the dispenser with the row of the plurality of different second reagents with the first row in the first target and actuating the dispenser to dispense the second reagents into the first row in the first target; and
aligning the dispenser with the row of the plurality of different second reagents with the second row in the second target and actuating the dispenser to dispense the second reagents into the second row in the second target.

10. The method of claim 9 wherein providing the dispenser with the plurality of different first reagents comprises providing the dispenser with the plurality of different first reagents arranged in first and second columns.

11. The method of claim 9 wherein providing the dispenser with the plurality of different second reagents comprises providing the dispenser with the plurality of different second reagents arranged in first and second rows.

12. The method of claim 9 wherein providing the first and second targets comprises providing a carrier tape including the first target and the second target.

13. The method of claim 9 wherein providing the dispenser with the plurality of different first reagents comprises:
providing a dispensing well plate including a plurality of nozzles arranged in the column of the dispenser;
providing the first reagent in a prep vial;
placing the prep vial relative to the dispensing well plate; and
drawing the first reagents from the prep vial to the plurality of nozzles arranged in the column of the dispenser.

* * * * *